United States Patent [19]

Kjellberg

[11] Patent Number: 5,423,787
[45] Date of Patent: Jun. 13, 1995

[54] SANITARY NAPKIN OR INCONTINENCE GUARD

[75] Inventor: Monica M. L. Kjellberg, Göteborg, Sweden

[73] Assignee: Molnlycke AB, Gothenburg, Sweden

[21] Appl. No.: 924,023

[22] PCT Filed: Mar. 26, 1991

[86] PCT No.: PCT/SE91/00228

§ 371 Date: Sep. 2, 1992

§ 102(e) Date: Sep. 2, 1992

[87] PCT Pub. No.: WO91/14415

PCT Pub. Date: Oct. 3, 1991

[30] Foreign Application Priority Data

Mar. 26, 1990 [SE] Sweden .................. 9001092

[51] Int. Cl.⁶ .................. A61F 13/15; A61F 13/20
[52] U.S. Cl. .................. 604/368; 604/358; 604/367; 604/372; 604/378; 604/385.1; 604/386
[58] Field of Search .................. 604/368, 385.1, 385.2, 604/358, 367, 368, 372, 378–380, 385.1, 386–387

[56] References Cited

U.S. PATENT DOCUMENTS

| 4,285,343 | 8/1981 | McNair | 604/385.1 |
| 4,333,462 | 6/1982 | Holtman et al. | 604/368 |
| 4,333,463 | 6/1982 | Holtman | 604/368 |
| 4,500,315 | 2/1985 | Pieniak et al. | 604/379 |
| 4,551,142 | 11/1985 | Kopolow | 604/368 |
| 4,559,050 | 12/1985 | Iskra | 604/368 |
| 4,596,567 | 6/1986 | Ishra | 604/368 |
| 4,699,619 | 10/1987 | Bernardin | 604/368 |
| 4,699,620 | 10/1987 | Bernardin | 604/368 |
| 4,838,885 | 6/1989 | Bernardin | 604/368 |
| 4,840,692 | 6/1989 | Kamstrup-Larsen | 604/368 |
| 4,857,065 | 8/1989 | Seal | 604/368 |
| 5,356,403 | 10/1994 | Faulks et al. | 604/358 |

FOREIGN PATENT DOCUMENTS

| 0217766 | 4/1987 | European Pat. Off. | |
| 0238334 | 9/1987 | European Pat. Off. | |
| 2176388 | 12/1986 | United Kingdom | 604/385.1 |
| 2227174 | 7/1990 | United Kingdom | |

Primary Examiner—Randall L. Green
Assistant Examiner—P. Zuttarelli
Attorney, Agent, or Firm—Young & Thompson

[57] ABSTRACT

The invention relates to an absorbent article, such as a sanitary napkin, a panty guard or an incontinence guard, comprising an absorbent pad enclosed in a casing (1, 2). The invention is characterized in that the absorbent body (3) comprises a first absorbent layer (5) which includes a mixture of hydrophilic fibers and superabsorbent material, and a second absorbent layer (6) of liquid-absorbent fiber material which is highly compressed and thereby has good liquid-spreading ability. The first absorbent layer (5) is placed on that side of the article which is intended to face towards the wearer in use, and the second absorbent layer (6) is in direct connection with the first absorbent layer (5) on that side of the article which is distal from the wearer in use.

10 Claims, 2 Drawing Sheets

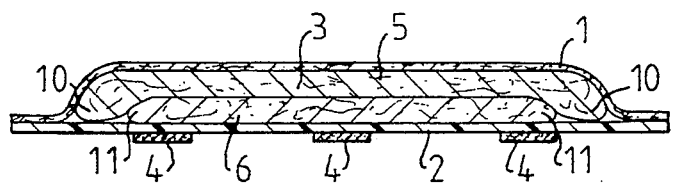
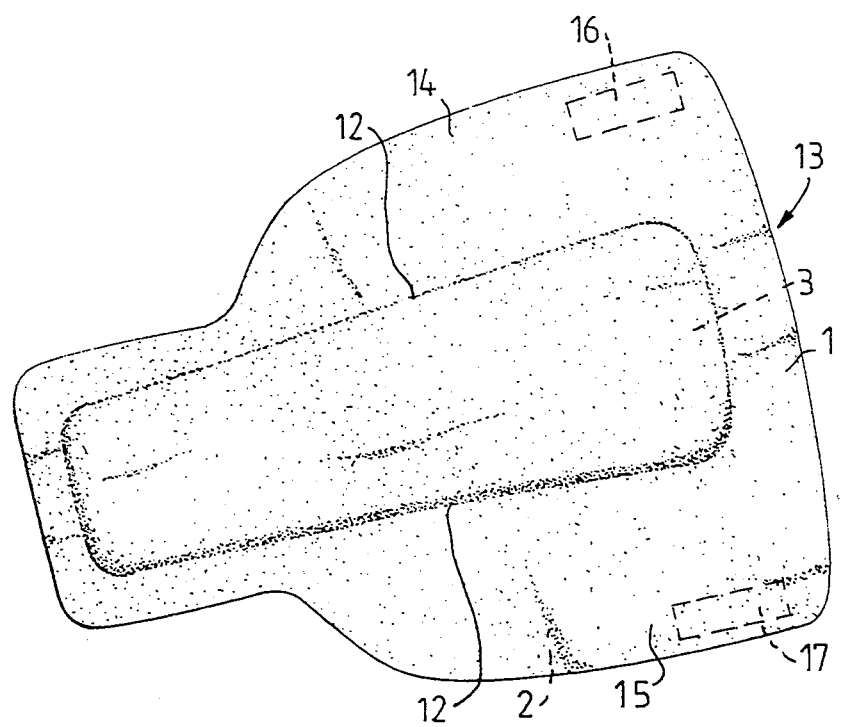

SANITARY NAPKIN OR INCONTINENCE GUARD

FIELD OF THE INVENTION

The present invention relates to an absorbent article, such as a sanitary napkin, a panty protector or an incontinence guard, comprising an absorbent body enclosed in a casing.

BACKGROUND OF THE INVENTION

Such articles are intended to be worn inside a pair of conventional underpants or panties, and are placed in the crotch of the underpants. The article is normally secured to the underpants with the aid of beads of pressure-responsive adhesive provided on the article.

One particularly serious problem with known articles of this kind is that they have an unacceptable high leakage frequency. In the case of sanitary napkins and panty protectors, such leakage can result in discolouration or total spoiling of the clothes worn by the person concerned, in addition to the physical discomfort that such leakage causes.

Normally, leakage occurs at the long side edges of the article. The reason for this is that such articles, as distinct from children's diapers or diapers for persons who suffer from heavy incontinence, must be configured with a relatively small width, in order for the article to fit in the space between the user's thighs. Liquid which impinges on and is absorbed by the article spreads in the article at essentially the same speed in all directions around the wetting point. Since such absorbent products as sanitary napkins and the like normally have an elongated rectangular shape, the liquid absorbed by the article will reach the side edges thereof long before the absorbency of the end parts of the article is utilized.

Another reason for side leakage with articles of this kind is that the article is heavily deformed in use. This deformation is most pronounced within those parts of the article that are located between the thighs of the wearer and thus subjected to mechanical forces by the wearer's thighs. This results in a further reduction in the width of the article within precisely that region which is intended to initially capture body fluid secreted by the wearer. Leakage may also occur because the article has been initially positioned wrongly inside the underpants, or because the article has moved to a wrong position in use.

One method of reducing the risk of leakage with sanitary napkins and the like is to compensate for the narrow width of the article in the crotch part of the wearer by heavily overdimensioning the absorbency of the article. This will also reduce, to some extent, the risk of leakage should the article be positioned wrongly in the underpants of the wearer.

However, this does not provide a wholly successful solution to the leakage problem. Absorbent articles of the kind meant here are normally provided with a cellulose-fluff absorbent pad, since fluff is a relatively cheap raw material and because it can be handled with well-tried manufacturing techniques. The primary drawback with the use of fluff as an absorption material is that its absorbency per unit of volume is relatively low. Consequently, products which are produced from cellulose fluff become, of necessity, thicker and more clumsy the greater the desired absorption capacity.

Articles such as sanitary napkins, panty protectors and guards for people suffering light incontinence are intended to be worn by adult, often healthy and working people. Consequently, it is required by the users that such articles will not be noticed when worn beneath conventional clothes, but which will nevertheless be leakage-proof. The article shall also be comfortable to wear and shall not chafe or otherwise irritate the skin of the wearer. In this respect, it is important that the surface of the article located nearest the wearer's skin will remain as dry as possible, even after absorbing body liquid. This cannot be achieved easily, particularly when the absorbent article is a sanitary napkin, since menstruation blood has a high viscosity and therefore tends to adhere to the surface of the napkin. So-called re-wetting is another problem which is particularly pronounced in both sanitary napkins and incontinence guards. Re-wetting means that body fluid which has already been absorbed by the absorbent pad is pressed by external forces back towards the skin of the wearer, for instance when the wearer sits down.

SUMMARY OF THE INVENTION

The present invention, however, provides an article of the kind defined in the introduction which essentially resolves the earlier mentioned problems associated with producing an absorbent article which is leakage-proof and discrete and which has low re-wetting tendencies.

The inventive article is primarily characterized in that the absorbent pad comprises a first absorption layer which includes a mixture of hydrophilic fibres and superabsorbent material, and a second absorption layer which comprises a highly compressible liquid-absorbing fibre material having good liquid spreading ability, wherein the first absorption layer is located on that side of the article which is intended to face towards the wearer in use and the second absorption layer is located in direct connection with the first absorption layer on that side of the article which is distal from the wearer in use.

Further features of the invention and advantages afforded thereby are set forth in the following Claims.

The combination of two absorption layers having mutually different absorption properties in accordance with the present invention provides a number of advantages.

The top layer, i.e. the layer which is intended to face towards the wearer in use, contains so-called superabsorbent material. By superabsorbent material is meant hydrophilic polymers which are capable of absorbing liquid corresponding to several times their own weight and which therewith swell to form a gel. Superabsorbent materials, or superabsorbents, are already known in different forms, for example in particulate, granulate, flake, film and fibre forms. The only requirement placed on the superabsorbent in respect of the present invention is that it can be mixed fairly uniformly with hydrophilic absorbent fibres, preferably in the form of cellulose fluff.

The primary purpose of the top absorbent layer is to allow secreted body fluid to pass rapidly down to the bottom layer, where the fluid spreads out. The layer shall also provide a barrier against rewetting caused by liquid being pressed back from the bottom absorption layer by forces applied externally to the article. Furthermore, liquid shall not spread in the plane of the layer. Distinct to what has earlier been usual, this is surprisingly achieved in accordance with the invention by placing the superabsorbent-containing layer nearest that side of the article which is intended to face towards the wearer in use. The superabsorbent functions to chemically bind the absorbed liquid in a gel form. This effectively prevents liquid from spreading around the wetting point in the top absorption layer. Since superabsorbents absorb liquid relatively slowly, the liquid is able to move away from the article surface before any appreciable amount of body liquid is absorbed in the top layer, this liquid transportation being effected gravitationally and by the differences in capillaries between the two absorption layers.

The bottom absorption layer, i.e. the layer which is intended to face away from the wearer in use, is compressed so as to function as a liquid-spreading layer in the article.

This compression results in compacting the fibres in the bottom layer, so that the space between adjacent fibres become smaller than the space between the fibres in the top layer. Since the space between adjacent fibres is of capillary magnitude and since liquid is always transported from coarser to finer capillaries, the absorbed body liquid will be transported actively from the top layer to the bottom layer. In this respect, it is particularly important that the two absorption layers are in direct connection with one another, so that the major part of the liquid will be transported in the depth or thickness extension of the article.

Another purpose of the bottom absorption layer is to spread the body liquid so that the absorbency of absorbent material distal from the region first wetted can also be utilized effectively. Liquid around the wetting point will be spread to a greater extent in the bottom layer than in the top layer, due to the high degree of compression of the material in said bottom layer. However, if the bottom layer is uniformly compressed and has essentially the same extend as the top layer, liquid will be spread equally in all directions around the wetting point. In this case, liquid will quickly reach the side edges of the article, resulting in leakage. Consequently, it is appropriate to provide the bottom layer with a compression pattern which changes the pattern in which liquid is spread, so that the liquid will disperse more in the longitudinal direction of the article than in its transverse direction. Such a pattern can be achieved, for instance, with longitudinally extending strips whose capillaries are finer than the capillaries of the surrounding absorbent material. Absorbed body liquid will therefore spread more quickly along the strips than in the surrounding material. The strips thus function to spread the liquid in the longitudinal direction of the article and also as barrier means which impede the transportation of liquid across the article. In order to avoid leakage at the edges of the article, however, it may be appropriate to terminate the compressed strips slightly inwardly of the short edges of the absorbent layer.

In some cases, for instance in the case of sanitary napkins and panty protectors, it may suffice to provide only one or a few compressed strips along the side edges of the bottom absorbent layer. This will primarily provide protection against side leakage, whereas the liquid will only spread to a smaller extent in the longitudinal direction of the article. Such leakage barriers can be supplemented with additional compression patterns, for instance of the kind described in Swedish Patent Specification No. 8804136-3.

When the bottom absorbent layer becomes saturated with body liquid, liquid from the bottom layer can again be absorbed in the top layer and bound in the superabsorbent material present in said top layer. Liquid which is pressed from the bottom absorbent layer back into the top layer, by external forces, is also absorbed by and bound in the top absorbent layer. An absorbent article which is constructed in accordance with the present invention will present a surprisingly dry and comfortable surface, even when worn for a comparatively long time.

A further advantage afforded by an absorbent article constructed in accordance with the invention is that it can be made very thin without loss of absorbency, and is therefore particularly suited for use by those who require a discrete and comfortable article. One problem with thin absorbent articles, however, is that they often become wrinkled or become deformed in some unsuitable manner when in use. Consequently, the articles should be relatively rigid, in order to withstand such deformation forces. It has been found that the bottom absorbent layer should have a rigidity or stiffness between 15.5 cm and 17.5 cm measured in accordance with SIS 650043. An article will present particularly good properties when the bottom layer has a rigidity of 16.5 cm according to SIS 650043. In this respect, the compressed, bottom absorbent layer of an inventive article can serve as means for preventing undesirable deformation of the article. With an article of this kind, the bottom layer is conveniently configured so as to be somewhat narrower and optionally also shorter than the top layer. The edge parts of the object will then be formed by the more lightly compressed and softer top absorbent layer. This will also avoid the risk of the article chafing the skin of the wearer.

BRIEF DESCRIPTION OF THE DRAWINGS

An inventive article will now be described in more detail with reference to an exemplifying embodiment thereof illustrated in the accompanying drawings.

FIG. 5 is a sectional view of a sanitary napkin according to a second embodiment of the invention; and FIG. 6 illustrates a sanitary napkin according to a third embodiment, seen from the side of the napkin which faces towards the wearer in use.

DETAILED DESCRIPTION OF THE INVENTION

Figure 1:
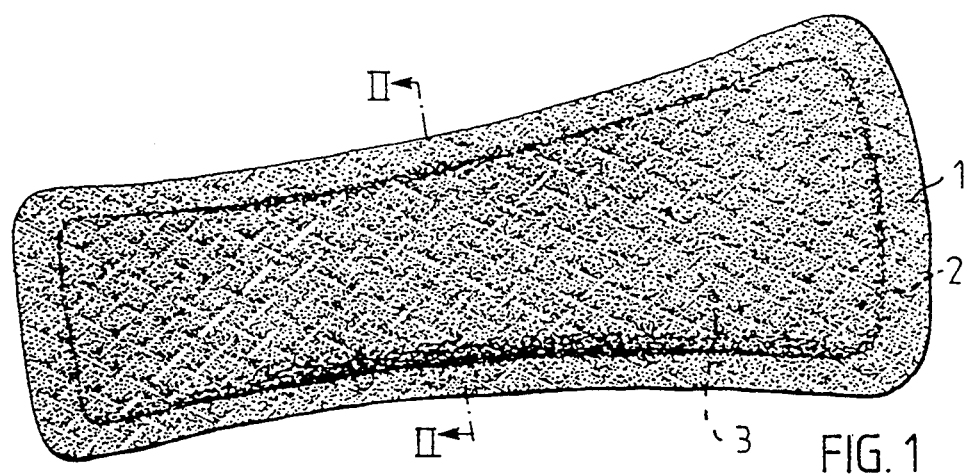
FIG. 1 is a top view of a sanitary napkin according to a first embodiment of the invention, seen from the side which faces the wearer in use.
Figure 2:
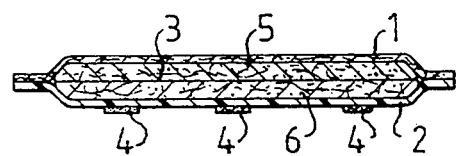
FIG. 2 is a sectional view of the sanitary napkin shown in FIG. 1, taken on the line II—II.

The sanitary napkin illustrated in FIGS. 1 and 2 includes a liquid-permeable first outer sheet 1, a liquid-impermeable second outer sheet 2, and an absorbent pad 3 enclosed between the two outer sheets. The liquid-permeable outer sheet 1 is intended to face towards the wearer in use. Suitable materials for these outer sheets are, for instance, different types of non-woven fabric or perforated plastic. The liquid-impermeable outer sheet or backing sheet 2 is provided with self-adhesive beads 4, by means of which the napkin can be secured inside a pair of panties. The liquid-impermeable sheet 2 may, for instance, consist of plastic film or non-woven fabric which has been treated so as to be impervious to liquid. The material from which the liquid-impermeable sheet is made may also be breatheable, so as to allow water vapour to pass through.

The absorbent pad 3 comprises two layers 5, 6. The first absorbent layer 5, which is the top layer in the Figure, includes a mixture of superabsorbent material and hydrophilic fibres, such as cellulose fluff. According to the present invention, an appropriate proportion of superabsorbent has been found to be between 10 and 50% of the total weight of the absorbent layer 5. A mixture which contains about 20% by weight superabsorbent has been found particularly suitable. An absorbent layer which comprises these proportions will exhibit a sufficient total absorbency and also good re-wetting and liquid-spreading properties.

The second absorbent layer 6, which is the bottom layer in the Figure, is compressed more heavily than the top absorbent layer 5 and contains essentially no superabsorbent material. The bottom absorbent layer 6 is preferably provided with a compression pattern, for instance the pattern illustrated in FIGS. 3 and 4, which will improve or enhance spreading of absorbed liquid in the longitudinal direction of the napkin.

Figure 3:
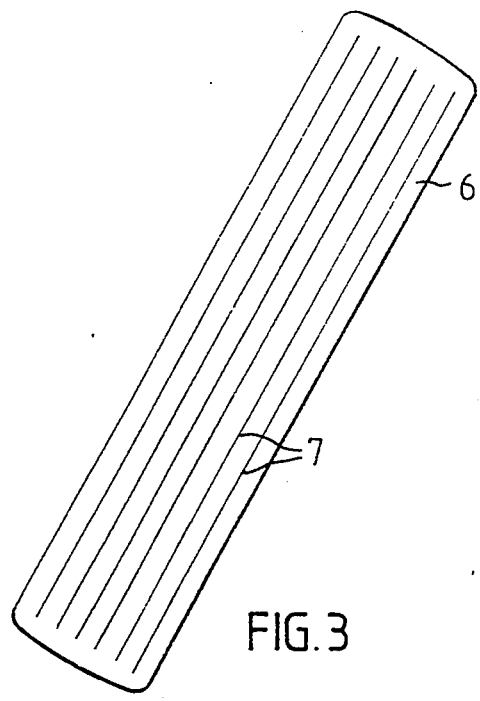
FIGS. 3 and 4 illustrate different embodiments of inventive liquid-transporting absorbent layers.

The absorbent layer 6 illustrated in FIG. 3 has a compression pattern which comprises a plurality of longitudinally extending lines 7 which function to spread liquid in their longitudinal directions but to impede the spreading of liquid perpendicularly thereto, in the manner described in the introduction.

Figure 4:
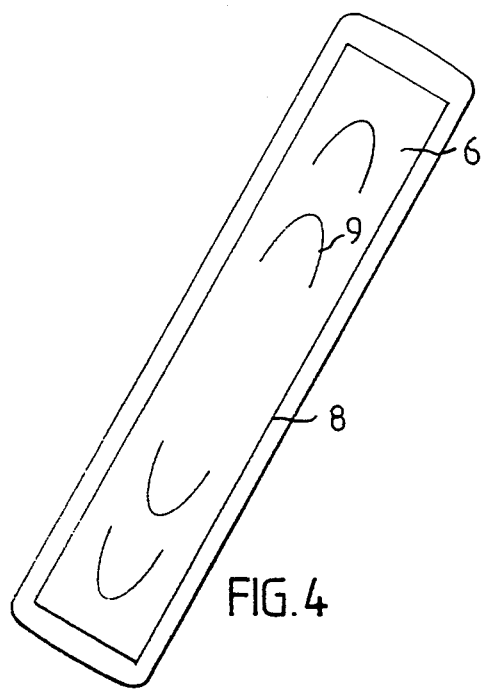

FIG. 4 illustrates an absorbent layer which is provided with liquid-barrier lines 8 along the edges thereof and also with a pattern of compression lines 9 inwardly of the barrier lines.

The napkin illustrated in FIG. 5 has essentially the same construction as the napkin illustrated in FIGS. 1 and 2. The reference numerals used in the FIG. 1 and 2 illustrations have therefore also been used to identify corresponding structural elements in the FIG. 5 illustration. The napkin illustrated in FIG. 5 differs from the napkin illustrated in FIGS. 1 and 2 in that the top absorbent layer 5 has a greater extension than the bottom absorbent layer 6. A napkin configured in this way will have soft, chafe-free edge parts 10 which also function as edge-leakage barriers. Absorbed liquid which reaches the edges 11 of the bottom layer 6 will be retarded by the outwardly projecting parts 10 of the top layer 5. This is due partly to the coarser capillary structure and therewith the slower transportation of liquid in the top layer 5, and partly because the top layer 5 contains superabsorbents which counteract the spreading of liquid by chemically binding the liquid absorbed.

When excreted body liquid is absorbed in an inventive sanitary napkin, the liquid will first penetrates down through the liquid-permeable sheet 1. The material from which this sheet is made should be of a kind which will ensure that substantially no liquid will be absorbed in the actual sheet itself. The liquid is then transported down through the top absorbent layer 5 of the absorbent pad. This liquid is transported partly gravitationally and partly by the capillary forces which remove the liquid by suction from the coarser capillaries in the top absorbent layer 5 to the finer capillaries in the bottom absorbent layer 6. A small part of the liquid will be absorbed in the top absorbent layer 5 as the liquid passes therethrough. Absorption and spreading of liquid in the top layer, however, is greatly limited by the fact that the liquid moves quickly through said layer. Furthermore, the combination of a loose, fluffy fibre structure and an admixture of superabsorbent results in a particularly effective barrier against the spreading of liquid within this layer 5.

When the liquid reaches the bottom absorbent layer 6 of more compact fibre-structure, the liquid is spread outwards within this layer. As described in the following, spreading of liquid in said layer can be controlled by providing a pattern of compression lines in the bottom layer 6. By spreading the liquid in the bottom layer 6, it is possible to utilize the absorbent material in said layer very extensively before the layer becomes saturated and part of the liquid is reabsorbed in the top absorption layer 5. Reabsorption of liquid in the top layer 5, and therewith utilization of this layer, can thereby take place over a much larger area than is otherwise possible with a superabsorbent layer of low liquid-spreading ability. It has earlier been thought meaningless to use superabsorbents in sanitary napkins, since the absorbency of the superabsorbents can only be utilized to a very low extent.

Menstruation blood namely has a high viscosity and spreads poorly in a conventional absorbent pad, as compared with urine for instance. If, in addition, the absorbent pad contains superabsorbent, which in itself hinders the spread of liquid, only the area around the wetting point on the napkin can be utilized for absorption purposes.

An appropriate superabsorbent chosen for inclusion in the top absorbent layer will swell as liquid is absorbed, in a manner to loosen the surrounding fibre structure and liquid will therefore be transported more quickly through the absorbent pad than when the absorbent pad is fresh and unused. A superabsorbent found to possess particularly suitable properties in this respect is Aqualic CA W3 from Nippon Shokubai KK Co. Ltd. Body liquid which is pressed back towards the liquid-permeable outer sheet by other factors will also be absorbed and bound by the superabsorbent in the top absorption layer.

Similar to the napkins illustrated in FIGS. 1, 2 and 5, the sanitary napkin illustrated in FIG. 6 comprises a liquid-permeable top sheet 1, a liquid-impermeable backing sheet 2 and an inventive absorbent pad 3 enclosed between said sheets.

The two outer sheets 1, 2 extend slightly beyond the longitudinal side edges 12 of the absorbent pad 3, at that end 13 of the napkin which is intended to lie forwardly on the wearer in use. Flexible side flaps 14, 15 are formed in this way on mutually opposite sides of the absorbent pad 3 at the forward part 13 of the napkin. In use, these side flaps are intended to be folded or wrapped around the bands or borders of the leg-openings of the user's underpanties and attached to the outside of such bands or borders by means of pressure-adhesive surfaces 16, 17 provided on the side flaps.

Because the invention enables the effective use of superabsorbents in sanitary napkins and incontinence guards, it is possible to produce extremely thin and highly absorbent articles. It is difficult, however, to prevent such articles from being deformed in use, such as to have a negative influence on their intended function. The flexible side flaps 14, 15 which are fastened around the leg-openings of the wearer's panties however, function to hold the napkin stretched over the genital region of the wearer, so as to avoid deformation in use.

Although the invention has been described in the aforegoing with reference to sanitary napkins, it will be understood that the invention can also be applied equally as well to panty protectors and incontinence guards. The invention is only limited to those areas of use which require particular regard to be taken to the size and shape of the article concerned.

An inventive article may also include stiffening means or the like and may have a configuration and attachment means other than those illustrated.

A number of embodiments are conceivable within the scope of the following Claims.

We claim:

1. An absorbent article comprising an absorbent pad enclosed in a casing, said casing having a first, liquid-permeable outer sheet and a second liquid-impermeable outer sheet and said pad being interposed between said first and second sheets, said pad being configured by a first and a second absorbent layer directly connected to each other, said first absorbent layer comprising a mixture of hydrophilic fibers and superabsorbent material, and being disposed immediately inside and in contact with said first liquid-permeable sheet, said second absorbent layer comprising a highly compressible liquid-absorbing fiber material, and being disposed beyond the first absorbent layer relative to the liquid-permeable sheet, and both said first and said second absorbent layers being compressed, said first absorbent layer being compressed to a lesser extent than said second absorbent layer, whereby said second absorbent layer exhibits superior liquid-spreading ability.

2. An article according to claim 1, wherein the first absorbent layer consists of a mixture of cellulose fluff and superabsorbent materials, and the second absorbent layer consists of cellulose fluff.

3. An article according to claim 1, wherein the first absorbent layer includes 10–50% by weight of superabsorbent material.

4. An article according to claim 1, wherein the second absorbent layer is narrower than the first absorbent layer.

5. An article according to claim 1, wherein the second absorbent layer is shorter than the first absorbent layer.

6. An article according to claim 1, wherein the second absorbent layer has a stiffness of between 15.5 cm and 17.5 cm measured according to SIS 650043.

7. An article according to claim 1, wherein the liquid-impermeable second outer sheet is disposed on that side of the article which in use is distal from the wearer, said first and second outer sheets being mutually connected around the absorbent pad and forming on both sides thereof outwardly projecting side flaps, said side flaps adapted to be folded around leg openings of a pair of panties, and said flaps including means of adhesive surfaces for attachment to said panties.

8. An article according to claim 1, wherein the second absorbent layer has at least two longitudinally extending compressed strips.

9. An article according to claim 8, wherein the compressed strips terminate inwardly of transverse edges of the second layer.

10. An article according to claim 8, wherein the second absorbent layer further includes compression lines disposed in a pattern inwardly of longitudinally-extending liquid barrier lines.

* * * * *